United States Patent [19]

Kaune

[11] 4,022,066
[45] May 10, 1977

[54] APPARATUS FOR REMOVING LIQUID SAMPLES

[75] Inventor: Manfred Kaune, Wendhausen, Germany

[73] Assignee: Diessel GmbH & Co., Hildesheim, Germany

[22] Filed: Oct. 7, 1975

[21] Appl. No.: 620,284

Related U.S. Application Data

[63] Continuation-in-part of Ser. No. 512,857, Oct. 7, 1974, Pat. No. 3,995,486.

[52] U.S. Cl. ............................................ 73/422 R
[51] Int. Cl.² .......................................... G01N 1/14
[58] Field of Search ......... 73/421 R, 421 B, 422 R; 251/141

[56] References Cited

UNITED STATES PATENTS

| | | |
|---|---|---|
| 2,589,712 | 3/1952 | Langsenkamp .................. 73/422 R |
| 3,450,353 | 6/1969 | Kekert ............................... 251/141 |
| 3,719,081 | 3/1973 | Lynn ................................. 73/421 B |

*Primary Examiner*—S. Clement Swisher
*Attorney, Agent, or Firm*—Gilbert L. Wells

[57] ABSTRACT

Apparatus for removing liquid samples, especially milk samples, from a flow facility wherein a feed pump, an electromagnetically actuated and normally closed metering valve physically located at a higher level than said feed pump, an air eliminator and a volume meter are sequentially arrayed downstream. The metering valve (7) is connected to flow line (6) by a short connecting pipe (15) sealed by closing element (11), the drain tube (8) of this valve leads to a sample container located above closing element (11) and defined by channel (14) traversed by valve shaft (13), which leaves annular gap (29) between the outer surface of the valve shaft (13) and the wall of channel (14) and which is large enough as to just suffice in cross-section to pass the amount of liquid sample to be removed.

13 Claims, 3 Drawing Figures

APPARATUS FOR REMOVING LIQUID SAMPLES

CROSS REFERENCE TO A RELATED APPLICATION

The present application is a Continuation-In-Part of application Ser. No. 512,857, filed Oct. 7, 1974 now U.S. Pat. No. 3,995,486.

BACKGROUND OF THE INVENTION

The present invention relates to apparatus for removing samples of liquids, especially milk, from a flow-metering facility, wherein a feed pump, an electromagnetically actuated metering valve closed in the rest position and at a higher lever than the pump, an air eliminator and a flow-metering instrument are sequentially arrayed in the downstream direction.

Application Ser. No. 512,857 and the references cited therein, namely U.S. Pat. Nos. 2,693,196; 2,703,190; 3,538,937 and 3,746,027 show the state of the art of flow-metering facilities comprising a feed pump, an air elimination and a flow-metering instrument sequentially arrayed in the downstream direction.

Apparatus for the purpose of continuously removing samples is required to monitor or to control, for instance as regards milk, the content in albumen or fat, the bacteriological condition, or the like.

In the apparatus of the prior art, a tap is opened, which is hooked to the feed line between the feed pump and the air eliminator, when the electromagnets and hence the metering valve are actuated, and a given amount of liquid discharges through this tap into the sample container during the opening of the metering valve. This prior art apparatus suffers from the drawback that a certain amount of liquid from the first discharge passing through the feed line remains in the metering valve after this one closes, which passes into the sample container as a sample of the subsequent (main) discharge and therefore spuriously affects the next sample of the next liquid discharge or even several subsequent samples. Depending on the number of samples associated with the individual discharges, this prior art apparatus does not always truly reflect the state of the subsequent discharge.

This spurious effect is especially significant when different suppliers are involved who provide milk to the same receiving facility and where there is a requirement to ascertain whether one or the other delivers milk of lesser quality or which is wholly unfit.

SUMMARY OF THE INVENTION

Accordingly the present invention addresses the problem of providing apparatus of the kind initially described which prevents spurious effects in the samples from ensuing liquid discharges and therefore ensures a genuine relationship between the samples and the associated discharges.

This problem is solved by the present invention in that the metering valve is connected to the feed line by a short connector that is sealed by the metering valve's closing element, the valve's drain tube leading to the sample container issuing above the closing element into a channel traversed by the valve shaft, and where the annular slot between the outer surface of the valve shaft and the channel wall is kept small enough that its cross-section just suffices for the flow of the liquid sample to be removed.

This arrangement allows reducing to a most minute quantity the residue from the previous liquid discharge, on account of the design and array of the metering valve, the order of magnitude of this residue being so selected that because of its minute percentge with respect to the next amount of sample, the latter cannot be spuriously affected, and differentiations and pertinent associations no longer are feasible. Because of the direct connection of the drain tube to the channel traversed by the valve shaft, the end of the channel being sealed by the closing element of the metering valve, additional dead spaces that might store liquid residues are prevented, so that residues may only remain in the annular gap between the channel wall and the outer surface of the valve shaft, and this gap may be kept correspondingly small.

In another prior art arrangement operating by means of an electromagnetically actuated metering valve, the latter is mounted behind the air eliminator, that is at its discharge end between the air eliminator and the liquid storing tank. This known arrangement suffers from the drawback that in this instance a segment of piping is involved which remains filled with liquid after the feed pump has been shut off, whereas the arrangement of the present invention provides for emptying the flow segment between feed pump and air eliminator in this case connected to the metering valve, after the feed pump is shut off. Mounting the metering valve between the air eliminator and the storage tank therefore causes spuriousness possibly of several subsequent samples because of the very large amount of liquid remaining in the segment, and therefore this known arrangement is quite incapable of solving the above-stated problem.

However, another possibility of solving the problem of the present invention consists in making use of the arrangement initially described and by mounting the metering valve with its shaft approximately perpendicularly to the flow line, and providing a control affecting the duration and frequency of the "open" times of the metering valve, whereby the latter at least may be actuated once again following termination of flow of a first amount of liquid.

Using such an arrangement, renewed actuation of the metering valve following flow shut off of a prior amount of liquid on one hand, and approximately a perpendicular array of the metering valve on the other, permit any residue still contained in the metering valve from the prior liquid to drain downward into the pipe segment empty at this intermediate stage, this segment being located between the feed pump and the air eliminator. Thus the metering valve itself is completely emptied upon renewed actuation, so that no liquid remains in it to spuriously affect the ensuing samples.

It is of special advantage in this respect if there is common application of the above cited steps for the purpose of solving the problem of the present invention, that is, bringing about a relatively small annular gap between channel wall and valve shaft on the one hand, and renewing the actuation of the metering valve following termination of a first flow of liquid on the other, because in this manner there is double reliability as to any spuriousness of the ensuing samples.

In the prior art arrangements, the electromagnet of the metering valve is designed as a lifting magnet engaging the valve shaft and lifting the closing element of the metering valve from its seat. On the other hand, as regards the present invention, a thrust magnet is used that pushes against the valve shaft in the open direction of the closing element, that is, it pushes the valve shaft down so that the closing element moving toward the flow line lifts from its seat. In this manner one obtains draining of the metering valve upon renewed actuation in especially simple manner.

The arrangement of the present invention furthermore provides the feasibility of easily replacing the metering valve because the latter is mounted at such a location of the apparatus that contains no liquid between two flow processes. This makes it possible for instance to assign each milk supplier a special and previously sterilized metering valve with drain tube, so that again residues from previous amounts are not misplaced. Especialy one prevents bacteria from previous samples multiplying in the metering valve and its connecting parts, which also would spuriously affect the sample analysis of the next flow.

It is to advantage in this respect that the closing element and valve shaft, together with the valve housing containing the drain tube, detachable from the electromagnet and its mounting and also is interchangeable with respect to the mounting and flow line. When this is done, only the closing element, together with its housing and the drain, need be replaced while the electromagnet and its mounting including all connections stay in the apparatus.

In order to easily separate the valve housing from the electromagnet, the latter advantageously is provided with a support screwed onto the valve housing, the pluger of the electromagnet passing through the support and the electromagnet acting on a cap connected to the free end of the valve shaft and subjected to the force of a return spring. When the support is removed, the electromagnet plunger simultaneously is detached without any further labor, so that the valve housing together with the drain tube may be removed and replaced.

Suitably the valve housing is provided with a threaded guide as a stop of the valve shaft so inserted as to be sealing and supporting the return spring. In this manner the fit between valve shaft and valve housing may be restricted to this guidance and an especially narrow annular gap between valve shaft and channel wall beyond the collar is achieved.

Advantageously, the control of the metering valve's electromagnet is provided with two time generators, one of which controls the individual switching pulses and the other of which their pulse width and hence the opening times of the metering valve. In order to obtain renewed actuation of the latter following termination of flow of a first quantity of liquid, the metering valve's electromagnet is acted upon together with the switch for turning off the feed pump and/or by means of the switch in the direction of opening. The metering valve therefore is opened if the feed pump is turned off and remains open until the feed pump is turned on again, so that draining of the metering valve into the main flow line is made possible in such manner.

A third time generator is provided to the same end, which upon shut off of the feed pump actuates the metering valve's electromagnet in the direction of opening, this third generator being hooked up through a special switch which also may be preferably actuated together with the feed pump turn off swich. When such a time generator is used, the metering valve opens only for a limited time following feed pump shut off, so that the valve's closing is ensured in proper time before the feed pump is turned on again.

Sometimes it is necessary for the purpose of removing the liquid residue from the metering valve's housing to obtain a pumping effect by actuating the metering valve several times in sequence. In such a case a synchronizing generator advantageously follows the third time generator, this synchronizer acting repeatedly in the direction of opening on the metering valve electromagnet following feed pump shut off.

The time generators and/or the synchronizer are adjustable regarding time and frequency of actuation so as to adapt to the particular equipment capacities to the consistency of the liquids flowing through. The time generators are RC circuits known per se.

Lastly, a time delay element is provided which prevents actuation of the metering valve following feed pump turn on until any residues in the main flow line from the previous liquid flow have been removed.

BRIEF DESCRIPTION OF THE DRAWINGS

The invention is discussed below by means of an embodiment shown in the drawings, wherein.

DESCRIPTION OF THE PREFERRED EMBODIMENTS

Figure 1:
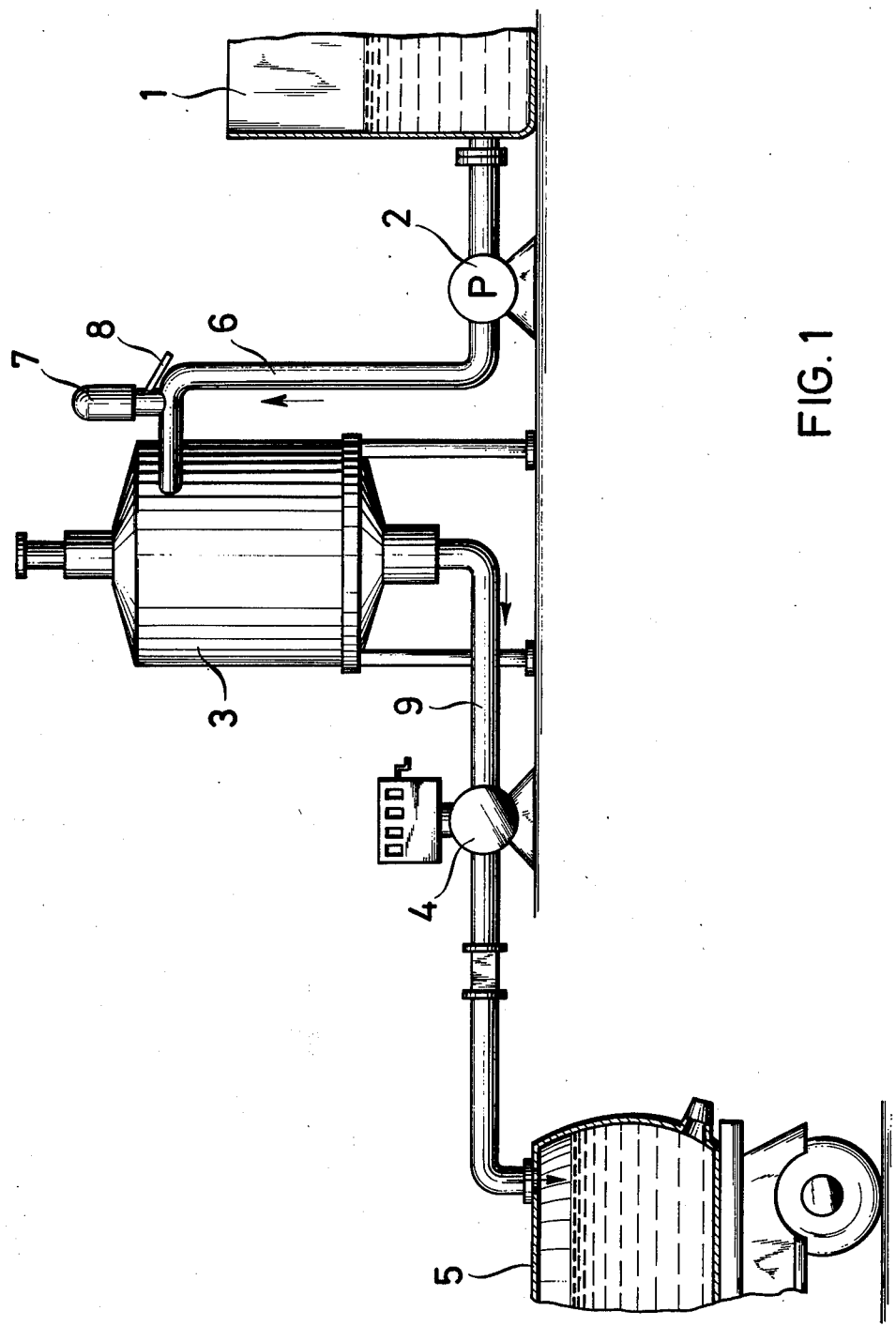
FIG. 1 shows schematically a flow metering facility to which the present invention applies.

FIG. 1 shows the flow metering facility, in which a tank 1 holding the liquid to be discharged, a feed pump 2, an air eliminator 3, a volume meter 4 and tank 5 receiving the liquid are sequentially arranged. A metering valve 7 with drain tube 8 leading to a sample container (not shown) is mounted in the feed line 6 between feed pump 2 and air eliminator 3 and near the latter, this valve being actuated electromagnetically and normally closed. As shown by FIG. 1, metering valve 7 is mounted as high as possible with respect to feed pump 2, so that upon termination of flow, the valve may drain when being actuated again upon termination of flow of a first quantity of liquid. As is seen from the figure, metering valve 7 is approximately perpendicular to the associated segment of flow line 6.

The location of metering valve 7 is the equipment is such that it is reliably drained when feed pump 2 is shut off. Such assurance is not necessarily provided as regards the pipe segment 9 between air eliminator 3 and volume meter 4.

Figure 2:
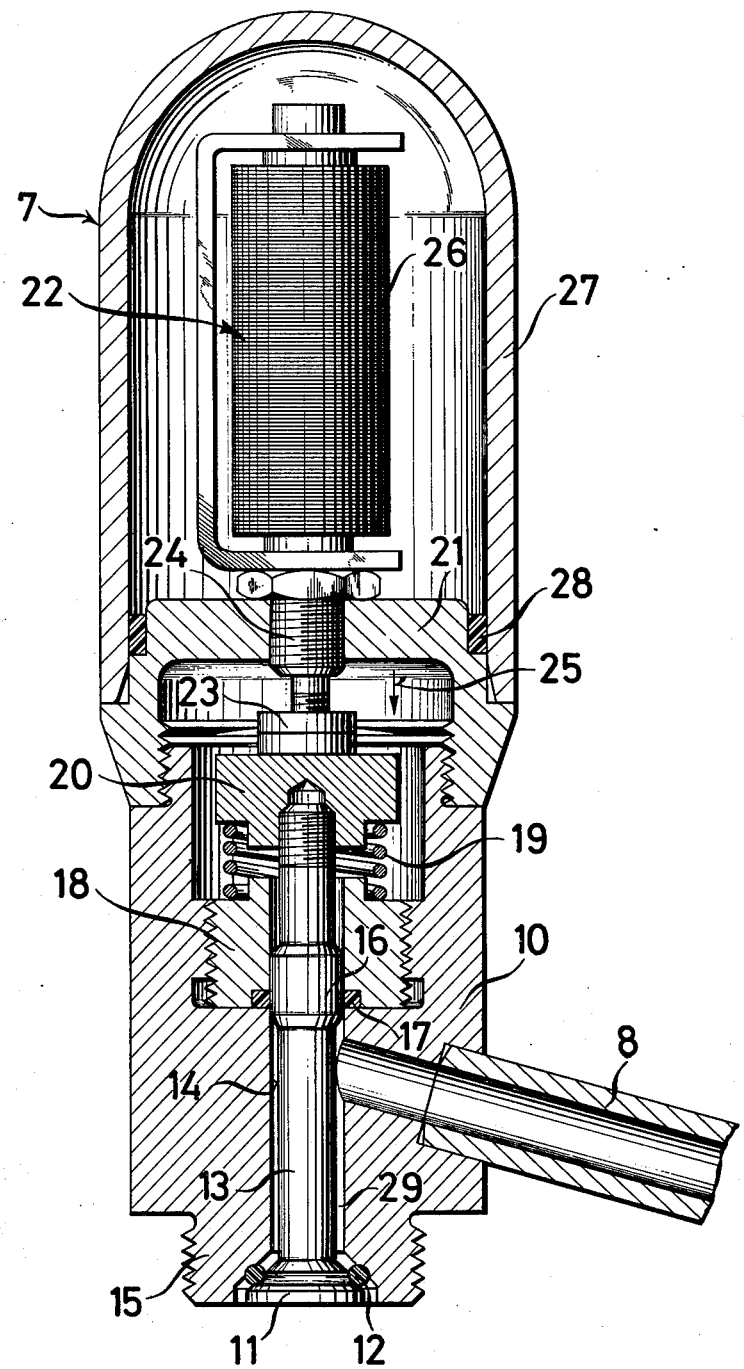
FIG. 2 shows a side view and section of the metering valve of the present invention.

FIG. 2 shows a section and side view of an embodiment of the metering valve 7 of the present invention. This valve consists of valve housing 10 of which closing element 11, together with a seal 12, are mounted at the lower end of housing 10, valve shaft 13 being located in a channel 14 into which issues drain tube 8. Valve housing 10 may be screwed by means of a short connector 15 into a corresponding connecting thread at flow line 6 (see FIG. 1).

Valve shaft 13 is provided with a stop 16 which with inserted seal 17 is guided in guide 18, the latter in turn being screwed into valve housing 10. A return spring 19 rests on guide 18, this spring acting on cap 20 connected to the upper end of valve shaft 13.

A support 21 for electromagnet 22 is screwed onto the upper end of valve housing 10, a bushing 24 of this electromagnet being screwed into support 21 for the purpose of guiding downward in the direction of arrow 25 plunger 23 of actuated electromagnet 22. When moving down, plunger 23 acts on cap 20 and hence on valve shaft 13, so that the valve will open.

Electromagnet 22 and its coil 26 are covered by a cap 27 and by a seal 28.

An annular gap 29 is formed between the outer surface of valve shaft 13 and the wall of channel 14, serving to let through to drain tube 8 the liquid sample entering at closing element 11. This annular gap 29 is kept small enough that its cross section just suffices for transmission of the liquid sample to be removed. As shown by FIG. 2, any residue in the metering valve may be located only in the annular gap between seal 12 and the orifice to drain tube 8, so that such a quantity will be very small.

Figure 3:
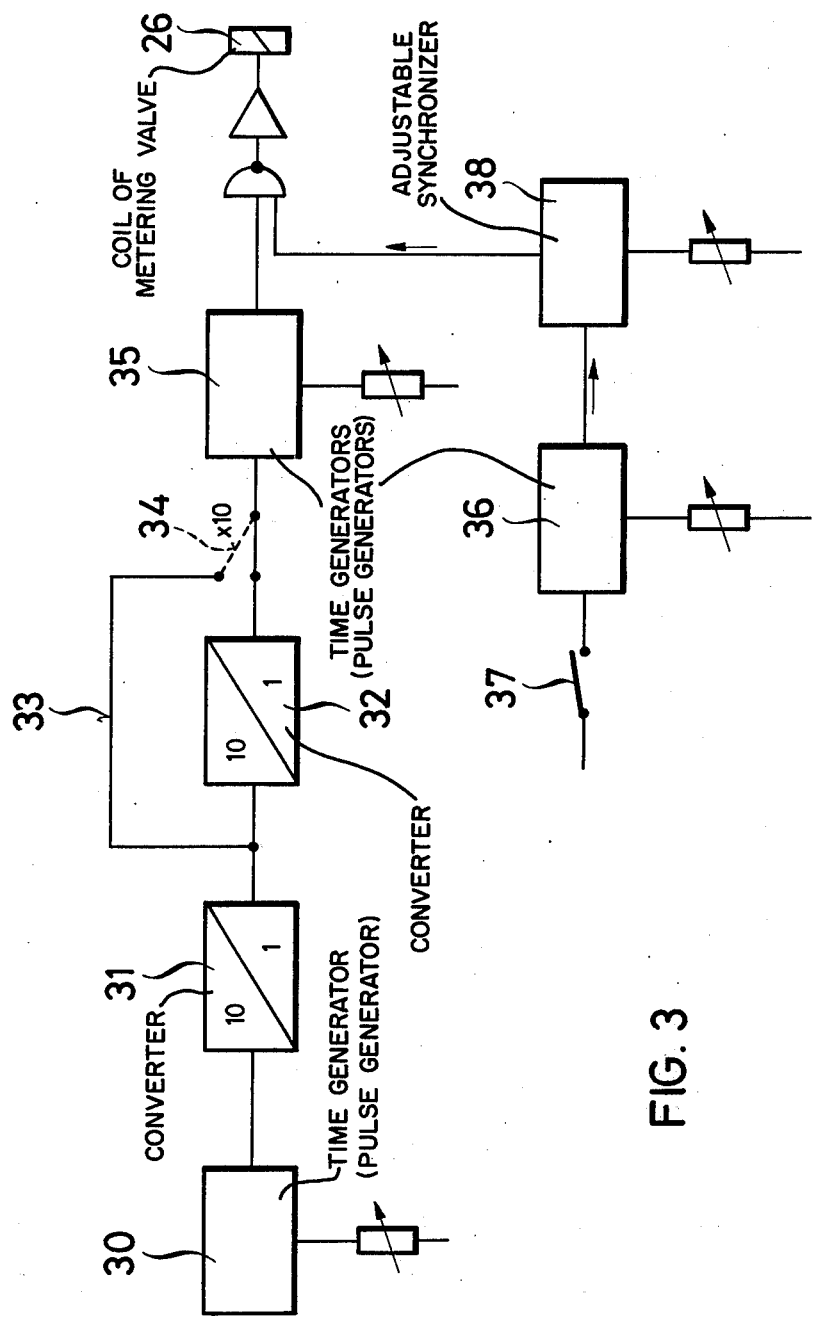
FIG. 3 is a diagrammatic block circuit for the control of the metering valve.

FIG. 3 shows the block circuit diagram for controlling the open times of the metering valve and for the control of the subsequent opening of the same valve following termination of transmission of a first quantity of liguid. As shown by FIG. 3, a first adjustable time generator 30 is provided for setting the time intervals between the individual switching pulses acting on coil 26 (see also FIG. 2) of the electomagnet. Two converters 31 and 32 follow time generator 30 and scale down the number of pulses to the ratio of 10 : 1. Manual conversion in the ratio of 10 : 1 is effected through connection 33 and switch 34. The pulses from the first time generator 30 are fed to a second time generator 35 controlling the duration of the individual open times of the metering valve, i.e., the duration of power being applied to coil 26 of the metering valve.

Lastly, a third time generator is provided which is actuated by a special switch 37 and and also acting on coil 26 of the electromagnet through an adjustable synchronizer 38. Special switch 37 may be ganged with or act together with the shut off switch for feed pump 2, so that when the latter is turned off, time generator 36 is activated and hence controls coil 26 of electromagnet 22 through synchronizer 38. Activating the latter results in actuating repeatedly in the direction of opening coil 26 of electromagnet 22 depending on the frequency set at synchronizer 38.

RC circuits known per se are used as time generators.

I claim:

1. In an apparatus for removing liquid samples, especially milk samples, from a flow system having a feed pump, an electro 0 magnetically actuated and normally closed metering valve physically located at a higher lever than said feed pump, an air eliminator and a volume meter sequentially arrayed downstream, the improvement comprising:
a flow line (6) connecting said feed pump and said air eliminator, said metering valve (7) connected to said flow line (6) by a short connecting pipe (15) and sealed by closing element (11), a drain tube (8) of said valve leading to a sample container issuing above said closing element (11) and defined by a channel (14) traversed by a valve shaft (13), and defining an annular gap (29) between the outer surface of said valve shaft (14) and a wall of said channel (14), said channel having a given cross section to pass the amount of liquid sample to be removed, said metering valve (7) and said valve shaft (13) vertically positioned, and control means (36,37,38) for adjusting the duration and the frequency of the openings of metering valve (7) are provided, said control means upon termination of flow of a first quantity of liquid allowing activating at least once more said metering valve (7).

2. Apparatus as defined in claim 1, wherein an electromagnet (22) actuates said metering valve (7) and is a thrust magnet acting on said valve shaft (13) in the direction of opening.

3. Apparatus as defined in claim 2, wherein said closing element (11) together with said valve shaft (13) and a valve housing (10) containing said drain tube (8) are separate and detachable from said electromagnet (22) and its mounting (21) and are exchangeable with respect to these and to flow line (6).

4. Apparatus as defined in claim 2, wherein said electromagnet (22) is connected to a support (21) screwed onto a valve housing (10) and traversed by a plunger (23) of said electromagnet, said plunger acting on a cap (20) connected to the free end of said valve shaft (13) and subject to the force of a return spring (19).

5. Apparatus as defined in claim 4, wherein said valve housing (10) is provided with a screwed-in guide (18) for a stop (16) of said valve shaft (13), said stop supporting said return spring (19).

6. Apparatus as defined in claim 1, wherein said control comprises first and second time generators (30,35) of which said first time generator (30) controls the time intervals between the individual switching pulses and said second time generator (35) controls the duration of the times of said metering valve (7).

7. Apparatus as defined in claim 6, wherein an electromagnet (22) of said metering valve (7) is actuated together with a feed pump turn off switch in the direction of opening.

8. Apparatus as defined in claim 7, wherein a third time generator (36) is provided which acts in the direction of opening on said electromagnet (22) of said metering valve (7) following turn off of a feed pump (2).

9. Apparatus as defined in claim 8, wherein said third time generator (36) is hooked up through a special switch (37) which is actuated together with a turn off switch of said feed pump.

10. Apparatus as defined in claim 9, wherein synchronizer (38) follows said third time generator (36) and acts repeatedly in sequence on said electromagnet (22) of said metering valve (7) following shut off of said feed pump (2).

11. Apparatus as defined in claim 10, wherein said time generators (30,35,36) and said synchronizer (38) are adjusted.

12. Apparatus as defined in claim 11, wherein said generators (30,35,36) are RC circuits.

13. Apparatus as defined in claim 12, wherein a time delay circuit is provided which following turning on feed pump (2) prevents any residue from the previous flow in feed line (6,9) from acting on metering valve (7) during and until removal of such residue.

* * * * *